(12) United States Patent
Esenwein et al.

(10) Patent No.: US 9,998,893 B2
(45) Date of Patent: Jun. 12, 2018

(54) MOBILE FUNCTION DEVICE (71) Applicant: Robert Bosch GmbH, Stuttgart (DE)

(72) Inventors: Florian Esenwein,
Leinfelden-Echterdingen (DE); Joachim Schadow, Stuttgart (DE); Joern Stock, Wernau (DE); Juergen Wiker, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 0 days. days.

(21) Appl. No.: 15/383,212

(22) Filed: Dec. 19, 2016

(65) Prior Publication Data

US 2017/0180965 A1    Jun. 22, 2017

(30) Foreign Application Priority Data

Dec. 21, 2015  (DE) .......................... 10 2015 226 194

(51) Int. Cl.
*H04M 3/00* (2006.01)
*H04W 4/22* (2009.01)
(Continued)

(52) U.S. Cl.
CPC .................. *H04W 4/22* (2013.01); *A61B 5/01* (2013.01); *A61B 5/1117* (2013.01); *A61B 5/681* (2013.01);
(Continued)

(58) Field of Classification Search
CPC .... G05B 19/048; G05B 19/058; G05B 15/02; H04W 76/007; H04W 4/22; H04W 88/02; H04M 1/72533; H04M 1/7253; H04M 1/72516; B25F 5/00; B23Q 11/0082; B23Q 11/0085
(Continued)

(56) References Cited

U.S. PATENT DOCUMENTS

| 6,362,778 | B2 * | 3/2002 | Neher ................... G01S 5/0018 |
| | | | 342/357.75 |
| 7,342,491 | B2 * | 3/2008 | Fujisawa .............. A61B 5/0002 |
| | | | 340/12.54 |

(Continued)

FOREIGN PATENT DOCUMENTS

| CA | 2 334 772 A1 | 12/1999 |
| CH | 697 402 B1 | 9/2008 |

(Continued)

*Primary Examiner* — Dai A Phuong
(74) *Attorney, Agent, or Firm* — Maginot, Moore & Beck LLP (57) ABSTRACT

The disclosure is a mobile tool-system function device that can be disposed on an extremity of an operator, having at least one sensor unit for sensing at least one operator-specific characteristic quantity and/or at least one position-specific characteristic quantity, and having at least one computing unit, which is designed to determine at least one state, in particular an emergency situation, in dependence on the at least one sensed operator-specific characteristic quantity and/or the at least one sensed position-specific characteristic quantity. The mobile function device further comprises at least one plausibility unit, which is designed to perform a plausibility check, in particular a plausibility check in respect of the presence of an emergency situation, in dependence on the at least one sensed operator-specific characteristic quantity and/or the at least one sensed position-specific characteristic quantity.

8 Claims, 2 Drawing Sheets

(51) Int. Cl.
  *G08B 21/02* (2006.01)
  *H04W 4/02* (2018.01)
  *G08B 21/04* (2006.01)
  *A61B 5/00* (2006.01)
  *A61B 5/01* (2006.01)
  *A61B 5/11* (2006.01)
  *B25F 5/00* (2006.01)

(52) U.S. Cl.
  CPC .............. *A61B 5/7282* (2013.01); *B25F 5/00* (2013.01); *G08B 21/02* (2013.01); *G08B 21/043* (2013.01); *G08B 21/0446* (2013.01); *G08B 21/0453* (2013.01); *H04W 4/021* (2013.01); *H04W 4/023* (2013.01); *A61B 5/683* (2013.01); *A61B 5/746* (2013.01); *A61B 2503/20* (2013.01); *A61B 2560/0214* (2013.01); *A61B 2562/0219* (2013.01)

(58) Field of Classification Search
  USPC .... 455/404.1–404.2, 418–420, 456.1–456.3, 455/457
  See application file for complete search history.

(56) References Cited

U.S. PATENT DOCUMENTS

| | | | |
|---|---|---|---|
| 8,618,930 B2* | 12/2013 | Papadopoulos | A61B 5/02427 340/539.11 |
| 9,445,396 B1* | 9/2016 | Herring | H04W 68/04 |
| 2010/0105427 A1* | 4/2010 | Gupta | H04M 1/72538 455/556.1 |
| 2012/0067931 A1* | 3/2012 | Yanosick | A45C 13/30 224/162 |
| 2012/0279742 A1* | 11/2012 | Roser | B25F 5/00 173/176 |
| 2013/0130735 A1* | 5/2013 | Roy | H04L 12/1818 455/518 |
| 2014/0107853 A1* | 4/2014 | Ashinghurst | G05B 19/048 700/297 |
| 2015/0081136 A1* | 3/2015 | Sutherland | G08B 21/043 701/2 |
| 2016/0094967 A1* | 3/2016 | Sulaiman | H04M 1/72541 455/404.2 |
| 2017/0008159 A1* | 1/2017 | Boeck | B25F 5/00 |
| 2017/0018007 A1* | 1/2017 | DeFrank | G06Q 30/0262 |
| 2017/0136875 A1* | 5/2017 | Logan | B60K 28/10 |
| 2017/0180536 A1* | 6/2017 | Stock | H04B 1/385 |
| 2017/0249824 A1* | 8/2017 | Kaplan | G08B 21/06 |

FOREIGN PATENT DOCUMENTS

| | | |
|---|---|---|
| DE | 198 32 361 A1 | 2/2000 |
| DE | 10 2013 221 128 A1 | 4/2015 |
| DE | 10 2015 206 608 A1 | 4/2016 |
| EP | 0 849 716 A2 | 6/1998 |
| EP | 1 702 560 A1 | 9/2006 |

\* cited by examiner

MOBILE FUNCTION DEVICE

This application claims priority under 35 U.S.C. § 119 to application no. DE 10 2015 226 194.8, filed on Dec. 21, 2015 in Germany, the disclosure of which is incorporated herein by reference in its entirety.

BACKGROUND

A mobile function device, which comprises at least one sensor unit for sensing at least one operator-specific characteristic quantity and/or at least one position-specific characteristic quantity, and which comprises at least one computing unit, which is designed to determine at least one burden state in dependence on the at least one sensed operator-specific characteristic quantity and/or the at least one position-specific characteristic quantity, is already known from EP 1 702 560 B1.

SUMMARY

The disclosure is based on a mobile function device, in particular a mobile tool-system function device that can be disposed on an extremity of an operator, having at least one sensor unit for sensing at least one operator-specific characteristic quantity and/or at least one position-specific characteristic quantity, and having at least one computing unit, which is designed to determine at least one state, in particular an emergency situation, in dependence on the at least one sensed operator-specific characteristic quantity and/or the at least one sensed position-specific characteristic quantity.

It is proposed that the mobile function device comprise at least one plausibility unit, which is designed to perform a plausibility check, in particular a plausibility check in respect of the presence of an emergency situation, in dependence on the at least one sensed operator-specific characteristic quantity and/or the at least one sensed position-specific characteristic quantity. The plausibility unit may be integrated into the computing unit, or realized as a separate unit that is connected to the computing unit, at least for exchange of data. A "computing unit" is to be understood to mean, in particular, a unit constituted by an evaluation unit and/or a control unit. The computing unit may be constituted both by only a processor and by a processor and further electronic components such as, for example, at least one storage means. The computing unit is preferably designed to evaluate at least one operator-specific characteristic quantity and/or position-specific characteristic quantity, sensed by means of the sensor unit, and to determine a state on the basis of the evaluation. For example, values that can be used for an evaluation are stored in a storage means of the computing unit. If, for example, a value of at least one operator-specific characteristic quantity and/or position-specific characteristic quantity, sensed by means of the sensor unit, corresponds to a stored value, the computing unit outputs, in particular, at least one electronic signal. The plausibility unit is preferably designed to check for plausibility, for example, of the signal output by the computing unit.

"Designed" is to be understood to mean, in particular, specially configured and/or equipped. That an element and/or a unit are/is designed for a particular function is to be understood to mean, in particular, that the element and/or the unit fulfill/fulfills and/or execute/executes this particular function in at least one application state and/or operating state.

A "mobile function device" is to be understood here to mean, in particular, a device that is designed, at least, to output, store, process and/or communicate data, in particular electronic data, and that, in particular, is realized so as to be unattached to a fixed location, such as, for example, realized so as to be movable, drivable, portable, transportable, or the like. An "operator-specific characteristic quantity" is to be understood here to mean, in particular, a characteristic quantity that defines at least one vital value of an operator, in particular of a wearer of the mobile function device, and/or that is dependent on a behavior of an operator, in particular of a wearer of the mobile function device. The operator-specific characteristic quantity may be realized as a type of operator-specific work burden such as, for example, as a force acting on an operator, as a noise burden, as a vibration burden or the like, as a vital value such as, for example, as a pulse of an operator, as a body temperature of an operator, as a fatigue characteristic quantity or the like, or as another operator-specific characteristic quantity considered appropriate by persons skilled in the art. A "position-specific characteristic quantity" is to be understood here to mean, in particular, a characteristic quantity that defines an orientation in space, a global position, a movement, or the like. The position-specific characteristic quantity may be realized as a cardinal point, as an orientation such as, for example, an inclination relative to a plane or the like, as a global position, or as another position-specific characteristic quantity considered appropriate by persons skilled in the art.

The sensor unit preferably comprises at least one sensor element that is designed to sense at least one position characteristic quantity, in particular at least one global position characteristic quantity, and/or at least one relative work-region position characteristic quantity. The sensor unit preferably comprises at least one position sensor element realized as a GPS sensor element, by means of which a global position of the mobile function device can be sensed. It is also conceivable, however, for the sensor unit to have a different position sensor element, considered appropriate by persons skilled in the art, for sensing a position characteristic quantity realized as a global position, such as, for example, a compass position sensor element, a Galileo position sensor element, a GLONASS position sensor element, a position sensor element, or the like. Preferably, the sensor unit has at least one sensor element realized as a work-region position sensor element, which is designed, for example by means of a propagation time measurement via a WLAN network or via a mobile telephony network, to enable a relative position of the mobile function device to be identified within a work region, such as, for example, an iBeacon locating element. It is possible, advantageously, to achieve sensing of a position of the mobile function device that, for example in the case of existence of an emergency situation, enables the location of the mobile function device, and thus of the wearer of the mobile function device, to be determined in a reliable manner.

It is conceivable that sensing of at least one position characteristic quantity is effected only when a hazard situation is identified. It is conceivable that sensing of at least one position characteristic quantity is deactivated during absence of a hazard situation.

Advantageously, the sensor unit comprises at least one temperature sensor element, which is designed to sense at least one temperature characteristic quantity, in particular a body temperature, of an operator.

Preferably, the sensor unit comprises at least one temperature sensor element realized as a body-temperature sensor element, which is designed to sense a body temperature of an operator on whom the mobile function device is disposed. In particular, the temperature sensor element realized as a body-temperature sensor element is preferably disposed on a body contact region of the mobile function device.

Preferably, the sensor unit comprises at least one temperature sensor element realized as an ambient-temperature sensor element, which is designed to sense an ambient temperature, in particular an ambient air temperature. In this case, the temperature sensor element realized as an ambient-temperature sensor element is preferably disposed on an outer region of the mobile function device. It is possible, advantageously, to sense a temperature characteristic quantity that can be used for evaluation in respect of a physical state of an operator with regard to a vital state. It is likewise conceivable that, at least as a result of a comparison of a value of the body-temperature sensor element and a value of the ambient-temperature sensor element, it is possible to deduce, for example, whether the mobile function device is being worn by an operator. Moreover, the values of the body-temperature sensor element and of the ambient-temperature sensor element can preferably be used for a plausibility check by the plausibility unit.

If, for example, it can be sensed by means of the sensor unit that the closure mechanism is closed and that there is a skin contact, values of the body-temperature sensor element and of the ambient-temperature sensor element can meaningfully be used for performing a plausibility check.

Advantageously, by means of the design of the mobile function device according to the disclosure, hazard situations can be reliably identified and a wearer of the mobile function device can advantageously be protected against hazards. Particularly advantageously, it is possible to avoid incorrect processing and/or output of data from the mobile function device. Particularly advantageously, a mobile function device that can provide a high degree of wearer safety can be made available.

Furthermore, it is proposed that the mobile function device have at least one communication unit for transmitting electronic data to at least one external unit, the at least one plausibility unit being designed to perform a plausibility check of the at least one sensed operator-specific characteristic quantity and/or of the at least one sensed position-specific characteristic quantity with electronic data that can be transmitted from the external unit by means of the communication unit. The communication unit is preferably realized as a wireless communication unit.

The communication unit may be realized as a WLAN communication unit, as a Bluetooth communication unit, as a radio communication unit, as an RFID communication unit, as an NFC unit, as an infrared communication unit, as a mobile telephony communication unit, as a Zigbee communication unit, or the like. Particularly preferably, the communication unit is designed for bidirectional data transmission. It is also conceivable, however, for the communication unit to be realized, alternatively or additionally, as a wired communication unit such as, for example, a LAN communication unit, a USB communication unit, as a Powerline communication unit, as a CAN-bus Communication unit, as an Ethernet communication unit, as a twisted-pair cable communication unit (CAT5 or CAT6), or the like. The terms "transfer", "transmit" and/or "communicate" are intended here to define, in particular, sending and/or receiving data, in particular electronic data. The communication unit can be used to transmit preferably electronic data between the mobile function device and the external unit, such as, for example, position data, emergency data and/or tripping data from a dead man's monitoring unit or the like. The external unit may be realized, for example, as a portable power tool, as an item of safety clothing, as a smartphone, as a laptop, as a PC, as a tablet PC, as a cloud, as an emergency control centre, as a service control centre, or the like. Preferably, by means of the plausibility unit, a plausibility check is effected taking account of operator-specific characteristic quantities and/or position-specific characteristic quantities sensed by means of the sensor unit, and of electronic data that can be transmitted from the external unit by means of the communication unit. Advantageously, a reliable comparison of data can be performed, in order to ensure that a situation has been correctly assessed. Advantageously, incorrect tripping, in particular incorrect tripping of an emergency signal, can be avoided, at least to a very large extent.

Further, it is proposed that the mobile function device comprise at least one optical and/or acoustic output unit, which is designed to output an optical and/or acoustic signal in dependence on a plausibility check performed by means of the at least one plausibility unit. Preferably, the output unit comprises at least one output element, which is realized as a display, as a loudspeaker, or the like. Preferably, a warning signal can be output by means of the output unit in dependence on a plausibility check performed by means of the at least one plausibility unit, in particular as a result of the presence of an emergency situation having been confirmed by the plausibility check.

The design according to the disclosure advantageously enables information to be output to an individual.

Thus, advantageously, an individual can be warned, for example, about a hazard situation. Moreover, advantageously, other individuals present in the area around the individual can likewise advantageously be warned, for example, about a hazard situation.

It is additionally proposed that the at least one sensor unit have at least one vital-data sensor element for sensing at least one operator-specific characteristic quantity realized as a vital characteristic quantity that can be processed by the at least one plausibility unit. If, for example, immobility, in particular a resting position, inactive state or the like of the mobile function device can be determined by means of the computing unit, in particular following a rapid movement of the mobile function device, an operator-specific characteristic quantity realized as a vital characteristic quantity, such as, for example, a body temperature, a pulse, a skin contact or the like can be used to check a plausibility in respect of the presence of an emergency situation. If it can be ascertained that, for example, there is no skin contact, it is plausible that the mobile function device has been voluntarily set down by an operator, and that an emergency situation such as, for example, a fall by an operator, or the like, does not exist. The design according to the disclosure makes it possible, advantageously, to achieve reliable evaluation of sensed characteristic quantities and reliable determination of states.

Furthermore, it is proposed that the at least one sensor unit have at least one acceleration sensor element for sensing at least one operator-specific characteristic quantity realized as an acceleration characteristic quantity that can be processed by the at least one plausibility unit. The acceleration sensor element may be realized as a multiaxial acceleration sensor element, in particular as a triaxial acceleration sensor element, as a rotation-rate sensor element, as a piezoelectric acceleration sensor element, as an acceleration sensor element constituted by a micro-electromechanical system (MEMS), or as another acceleration sensor element considered appropriate by persons skilled in the art. The design according to the disclosure advantageously makes it possible for an operator-specific characteristic quantity, that preferably allows inferences to be made concerning an orientation and/or movement of an operator, to be determined in an inexpensive manner.

Moreover, advantageously, an acceleration characteristic quantity sensed by means of the acceleration sensor element can be used to evaluate the presence of a free fall, for example from a ladder, or the like. Moreover, advantageously, an acceleration characteristic quantity sensed by means of the acceleration sensor element can be used to identify whether an operator is in a hazardous situation, in particular if the acceleration sensor element does not sense any movement, and an operator on whom the mobile function device is disposed does not change position over a defined period of time, in particular an at least substantially horizontal position, relative to a ground.

Further, it is proposed that the mobile function device have at least one acknowledgement unit, which is designed to be actuated by an operator in dependence on a plausibility check performed by means of the at least one plausibility unit. If, for example, an emergency situation is identified as a result of a plausibility check having been performed, an operator can be notified of this by means of the output unit.

Should an operator fail to actuate the acknowledgement unit within a predefined time span such as, for example, within a time span of five to ten seconds, following an output of a notification, an emergency signal is output by means of the output unit, and an emergency call is transmitted via the communication unit. Advantageously, a probability of the issuing of a false alarm can be kept small, at least to a very large extent.

It is additionally proposed that the mobile function device comprise at least one fastening unit at least for fastening the at least one sensor unit to an extremity of an operator. Preferably, the fastening unit comprises at least one armband for fastening the at least one sensor unit to an extremity of an operator. Alternatively, however, it is also conceivable for the fastening unit to be provided on an upper part of the body, in particular in a chest region, of an operator for the purpose of fastening the at least one sensor unit. The fastening unit is designed, in particular, to enable the sensor unit, the communication unit and the plausibility unit to be disposed on an extremity of an operator. Preferably, the sensor unit, the computing unit and/or the plausibility unit are/is disposed, at least partially, in a housing of the mobile function device that is disposed on the fastening unit, or disposed, at least partially, in or on the arm-band of the fastening unit. Advantageously, the design according to the disclosure makes it possible to achieve reliable sensing of at least one operator-specific characteristic quantity. It is made possible, advantageously, for at least the sensor unit to be easily fastened to an extremity of an operator.

Additionally proposed is a system, in particular a handheld power tool system, having at least one mobile function device according to the disclosure and having at least one external unit, the external unit having at least one sensor unit, which is designed, at least, to sense at least one operator-specific characteristic quantity and/or at least one position-specific characteristic quantity. The external unit is preferably realized as a portable power tool. A "portable power tool" is to be understood here to mean, in particular, a power tool, for performing work on workpieces, that can be transported by an operator without the use of a transport machine. In particular, the portable power tool has a mass of less than 40 kg, preferably less than 10 kg, and particularly preferably less than 5 kg. Preferably, safety functions of the portable power tool and/or safety functions power-tool accessory units that can be disposed on the portable power tool, such as, for example, a kick-back parameter, a maximum torque, a maximum rotational speed, a percussion energy, a protective hood position and/or a ratchet coupling release moment can be controlled by open-loop and/or closed loop control on the basis of the at least one operator-specific characteristic quantity and/or on the basis of the at least one position-specific characteristic quantity, preferably by means of an open-loop and/or closed-loop control unit of the portable power tool. The safety functions in this case are preferably dependent on a power tool type of the portable power tool. It is also conceivable, however, for the external unit to be of a different design, considered appropriate by persons skilled in the art, such as, for example, designed as a smartphone or the like. Advantageously, in the case of the external unit being designed as a portable power tool, convenient setting of safety functions can be achieved. Moreover, advantageously, a high degree of safety of an operator of a portable power tool can be achieved.

Further, it is proposed that the at least one plausibility unit be designed to perform a plausibility check of the at least one sensed operator-specific characteristic quantity and/or of the at least one sensed position-specific characteristic quantity of the sensor unit of the mobile function device, with at least one sensed operator-specific characteristic quantity and/or with at least one sensed position-specific characteristic quantity of the sensor unit of the external unit that can be transmitted from the external unit to the mobile function device by means of a communication unit of the mobile function device. Advantageously, the design according to the disclosure makes it possible to achieve a reliable determination of a state, in particular an emergency situation.

Additionally proposed is a method for identifying an emergency situation by means of a method according to the disclosure, in which there is effected, in at least one method step, a plausibility reconciliation of electronic data, in particular of at least one sensed operator-specific characteristic quantity and/or of at least one sensed position-specific characteristic quantity, of the mobile function device and of electronic data, in particular of at least one sensed operator-specific characteristic quantity and/or of at least one sensed position-specific characteristic quantity, of the external unit. Advantageously, by means of the method according to the disclosure, hazard situations can be reliably identified and an operator can advantageously be protected against hazards.

Particularly advantageously, it is possible to avoid incorrect processing and/or output of data. Particularly advantageously, a method that can provide a high degree of wearer safety can be made available.

The mobile function device according to the disclosure, the system according to the disclosure and/or the method according to the disclosure are/is not intended in this case to be limited to the application and embodiment described above. In particular, the mobile function device according to the disclosure, the system according to the disclosure and/or the method according to the disclosure may have individual elements, components and units, and method steps, that differ in number from a number stated herein, in order to fulfill a principle of function described herein. Moreover, in the case of the value ranges specified in this disclosure, values lying within the stated limits are also to be deemed as disclosed and applicable in any manner.

BRIEF DESCRIPTION OF THE DRAWINGS

Exemplary embodiments of the disclosure are presented in the drawings an are explained in more detail in the description below.

In the drawings.

DETAILED DESCRIPTION

Figure 1:
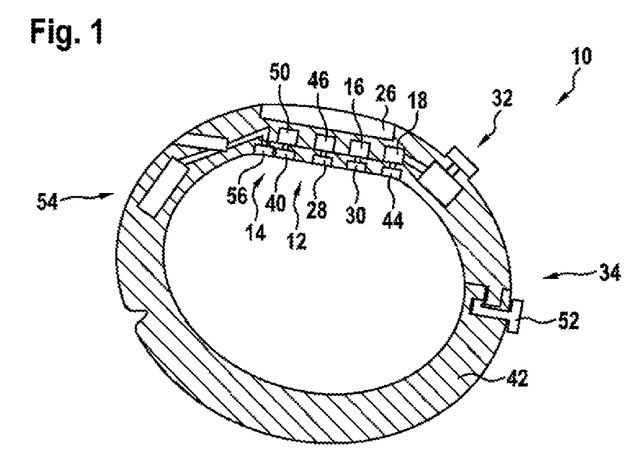
FIG. 1 shows a sectional view of a mobile function device according to the disclosure, in a schematic representation.
Figure 2:
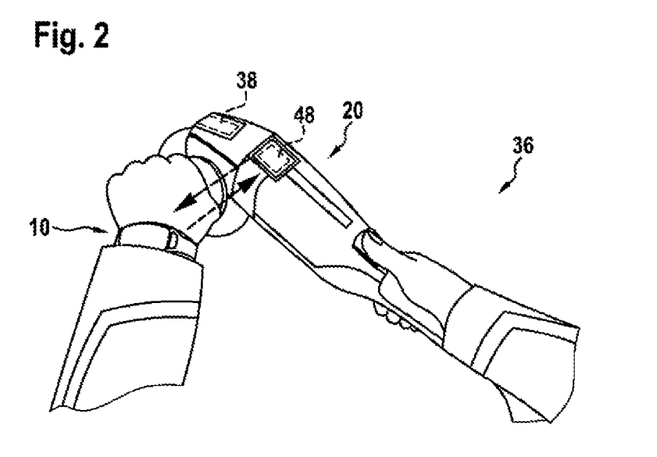
FIG. 2 shows a system according to the disclosure, comprising the mobile function device according to the disclosure, and at least one external unit, realized as a portable power tool, in a schematic representation.
Figure 3:
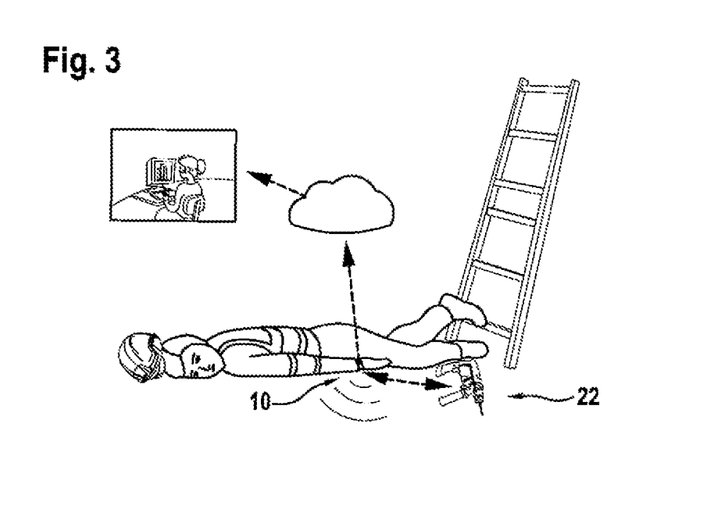
FIG. 3 shows the system according to the disclosure, comprising the mobile function device according to the disclosure, and comprising at least one external unit, realized as an alternative portable power tool, during the occurrence of an emergency situation, in a schematic representation.
Figure 4:
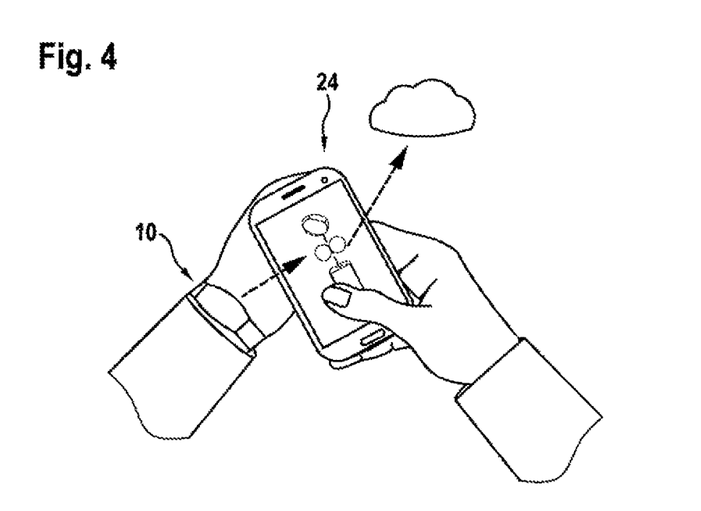
FIG. 4 shows the system according to the disclosure, comprising the mobile function device according to the disclosure, and comprising at least one external unit, realized as a smartphone, in a schematic representation.

FIG. 1 shows a sectional view of a mobile function device 10. The mobile function device 10 is realized such that it can be disposed on a part of the body of an operator, in particular on an extremity of an operator (FIGS. 2 to 4). The mobile function device 10 is realized, in particular, as a mobile tool-system function device that can be disposed on an extremity of an operator. The mobile function device 10 is preferably realized as a smartband. The mobile function device 10 is preferably realized such that it can be disposed on an arm of an operator (FIGS. 2 to 4). The mobile function device 10 comprises at least one sensor unit 12 for sensing at least one operator-specific characteristic quantity and/or at least one position-specific characteristic quantity, and at least one computing unit 14, which is designed to determine at least one state, in particular at least one emergency situation, in dependence on the at least one sensed operator-specific characteristic quantity and/or the at least one sensed position-specific characteristic quantity. The mobile function device 10 comprises at least one fastening unit 34, at least for fastening the at least one sensor unit 12 to an extremity of an operator (FIGS. 2 to 4).

The fastening unit 34 has at least one fastening element 42, which is designed to be disposed on the part of the body of an operator. In the exemplary embodiment represented in FIGS. 1 to 4, the fastening element 42 is realized as an arm-band. The fastening element 42 may be realized as an elastic arm-band, as a link arm-band, as a metal arm-band, as a plastic arm-band, or the like. It is also conceivable, however, for the fastening element 42 to be of a different design, considered appropriate by persons skilled in the art, such as, for example, designed as an ankle band, as a chest belt or the like. The fastening unit 34 preferably has at least one closure element 52, which is designed to connect to each other at least two regions of the fastening element 42 that are movable relative to each other, by means of a positive and/or non-positive connection. The closure element 52 may be of any design considered appropriate by persons skilled in the art, such as, for example, designed as a hook-and-loop closure, as a press-button, as a folding clasp, as a snap-in closure, or the like. The regions of the fastening element 42 that are movable relative to each other are preferably mounted so as to be movable relative to each other by means of a joint or by means of a hinge. The joint or the hinge may be of any design considered appropriate by persons skilled in the art, such as, for example, designed as a film hinge, as a pin hinge, or the like. It is also conceivable, however, for the fastening element 42 to be realized as an elastic arm-band that, as a result of an elastic deformation, can be moved over a hand of an operator and disposed on an arm of an operator. In the case of the fastening element 42 being designed as an elastic arm-band, the fastening unit 34 is preferably realized such that it is separate from the closure element 52 and from the joint or hinge. The sensor unit 12 and/or the computing unit 14 are/is at least partially integrated in the fastening element 42, or at least partially disposed in a housing (not represented in greater detail here) of the mobile function device 10 that can be fixed to the fastening element 42.

The computing unit 14 is preferably designed to evaluate at least one operator-specific characteristic quantity and/or position-specific characteristic quantity sensed by means of the sensor unit 12, and to determine a state on the basis of the evaluation.

For example, values that can be used for an evaluation and/or assessment of the at least one operator-specific characteristic quantity and/or position-specific characteristic quantity sensed by means of the sensor unit 12 are stored in a storage means 40 of the computing unit 14. If, for example, a value of at least one operator-specific characteristic quantity and/or position-specific characteristic quantity sensed by means of the sensor unit 12 corresponds to, is below or exceeds a stored value, the computing unit 14 outputs at least one electronic signal, in particular at least one electronic signal that defines a state. The operator-specific characteristic quantity may be realized as a type of operator-specific work burden such as, for example, as a force acting on an operator, as a noise burden, as a vibration burden or the like, as a vital value such as, for example, as a pulse of an operator, as a body temperature of an operator, as a fatigue characteristic quantity or the like, or as another operator-specific characteristic quantity considered appropriate by persons skilled in the art.

The position-specific characteristic quantity may be realized as a cardinal point, as an orientation such as, for example, an inclination relative to a plane or the like, as a global position, or as another position-specific characteristic quantity considered appropriate by persons skilled in the art.

The mobile function device 10 comprises at least one plausibility unit 16, which is designed to perform a plausibility check, in particular a plausibility check in respect of the presence of an emergency situation, in dependence on the at least one sensed operator-specific characteristic quantity and/or the at least one sensed position-specific characteristic quantity.

It is checked by means of the plausibility unit 16, preferably in dependence on the at least one sensed operator-specific characteristic quantity and/or the at least one sensed position-specific characteristic quantity, whether a state identified by the communication unit 14 is plausible. Advantageously, hazard situations can be reliably identified and a wearer of the mobile function device 10 can advantageously be protected against hazards. Particularly advantageously, it is possible to avoid incorrect processing and/or output of data from the mobile function device 10.

The mobile function device 10 comprises at least one optical and/or acoustic output unit 26, which is designed to output an optical and/or acoustic signal in dependence on a plausibility check performed by means of the at least one plausibility unit 16. For example, differing temperature characteristic quantities can be displayed by means of the output unit 26, the output unit 26 comprising at least one output element realized as a display and/or one output element realized as an illuminated element, in particular as an LED.

For example, a measured body temperature of an operator who is wearing the mobile function device 10 on the arm, and/or an ambient temperature, can be displayed, in particular in colored gradations. Advantageously, in the case of an impending hazard, a warning message can be output by means of the output unit 26. Further items of information, considered appropriate by persons skilled in the art, can be output by means of the output unit 26.

For the purpose of energy supply, the mobile function device 10 comprises at least one energy conversion unit 54. The energy conversion unit 54 may be realized as a piezoelectric energy conversion unit, as a solar energy unit, or the like. In the case of the energy conversion unit 54 being designed as a piezoelectric energy conversion unit, it is conceivable for at least one piezoelectric element to be disposed in or on the fastening element 42, and to convert motion energy into electrical energy as a result of a deformation of the fastening element 42. It is conceivable for the piezoelectric energy conversion unit to have a multiplicity of piezoelectric elements, which are disposed in or on the fastening element 42. Alternatively or additionally, the energy conversion unit 54 may be realized as an inductive energy supply unit or as a cable energy supply unit. In addition, the energy conversion unit 54 is connected to an energy storage unit 56 of the mobile function device 10, in a manner already known to persons skilled in the art, by means of an energy supply line (not represented in greater detail here). The energy storage unit 56 is realized, in particular, as a storage battery unit.

The energy storage unit 56 may be disposed in a replaceable manner on the fastening unit 34. The energy storage unit 56 preferably comprises at least one backup unit, which is designed to enable basic functions of the mobile function device 10 in an emergency operating mode, such as, for example, output of a message by means of the output unit 26 in the case of a low energy content of the energy storage unit 56, or the like.

The at least one sensor unit 12 has at least one vital-data sensor element 28 for sensing at least one operator-specific characteristic quantity realized as a vital characteristic quantity that can be processed by the at least one plausibility unit 16. The vital-data sensor element 28 may be realized to sense a pulse, a temperature characteristic quantity, in particular a body temperature of an operator, or the like. The at least one sensor unit 12 has at least one acceleration sensor element 30 for sensing at least one operator-specific characteristic quantity realized as an acceleration characteristic quantity that can be processed by the at least one plausibility unit 16.

Preferably, an orientation of the mobile function device 10 in space, the presence of a movement of the mobile function device 10, or other state or characteristic quantity considered appropriate by persons skilled in the art can be determined by means of the computing unit 14 on the basis of sensing of at least one operator-specific characteristic quantity, realized as an acceleration characteristic quantity, by the acceleration sensor element 30. The sensor unit 12 preferably comprises at least one position sensor element 44, which is designed to sense at least one position characteristic quantity, in particular at least one global position characteristic quantity.

Preferably, the sensor unit 12 has at least one work-region position sensor element 46, which is designed, for example by means of a propagation time measurement via a WLAN network or via a mobile telephony network, to enable a relative position of the mobile function device 10 to be identified, in particular within a work region. The work-region position sensor element 46 may be realized, for example, as an iBeacon locating element. Preferably, the sensor unit 12 comprises at least one ambient-temperature sensor element 50, which is designed to sense an ambient temperature, in particular an ambient air temperature. The sensor unit 12 may have further sensor elements, considered appropriate by persons skilled in the art, that are designed to sense at least one operator-specific characteristic quantity and/or at least one position-specific characteristic quantity.

The mobile function device 10 has at least one acknowledgement unit 32, which is designed to be actuated by an operator in dependence on a plausibility check performed by means of the at least one plausibility unit 16. If, for example, an emergency situation is identified as a result of a plausibility check having been performed, an operator can be notified of this by means of the output unit 26. Should an operator fail to actuate the acknowledgement unit 32 within a predefined time span such as, for example, within a time span of five to ten seconds, following an output of a notification, an emergency signal is output by means of the output unit 26, and/or an emergency call is transmitted via a communication unit 18 of the mobile function device 10.

FIG. 2 shows a system 36, comprising the mobile function device 10, and comprising at least one external unit 20, which has at least one sensor unit 38 that is designed to sense at least one operator-specific characteristic quantity and/or at least one position-specific characteristic quantity.

In FIG. 2, the external unit 20 is realized as a portable power tool, in particular as an angle grinder.

In FIG. 2, the external unit 20 realized as a portable power tool is realized exemplarily as an angle grinder. It is also conceivable, however, for the external unit 20, realized as a portable power tool, to be realized as a different power tool, considered appropriate by persons skilled in the art, such as, for example, as a circular saw, as a power drill, as a percussion power drill, as a hammer drill and/or chipping hammer, or the like. For the purpose of communicating with the communication unit 18 of the mobile function device 10, the external unit 20 realized as a portable power tool comprises at least one counter-communication unit 48, which is realized so as to correspond to the communication unit 18 of the mobile function device 10, at least in respect of a data transmission method. By means of a combined action of the counter-communication unit 48 and the communication unit 18, sensed characteristic quantities can be transmitted between the mobile function device 10 and the external unit 20 realized as a portable power tool. The mobile function device 10 has at least the communication unit 18 for transmitting electronic data, at least to the external unit 20 realized as a portable power tool, or to further external units 22, 24, the at least one plausibility unit 16 being designed to perform a plausibility check of the at least one sensed operator-specific characteristic quantity and/or of the at least one sensed position-specific characteristic quantity with electronic data that can be transmitted from the external unit 20 by means of the communication unit 18. The at least one plausibility unit 16 is designed to perform a plausibility check of the at least one sensed operator-specific characteristic quantity and/or of the at least one sensed position-specific characteristic quantity of the sensor unit 12 of the mobile function device 10, with at least one sensed operator-specific characteristic quantity and/or with at least one sensed position-specific characteristic quantity of the sensor unit 38 of the external unit 20, 22, 24 that can be transmitted from the external unit 20, 22, 24 to the mobile function device 10 by means of the communication unit 18 of the mobile function device 10. An optical and/or acoustic feedback, as to whether the communication unit 18 is connected to an external unit 20, 22, 24, can be output by means of the output unit 26. Thus, advantageously, an operator can ascertain whether a communication connection has been reliably effected. In addition, it is conceivable for the type of external unit 20, 22, 24, to which the communication unit 18 is connected and with which it communicates, to be to be displayed to an operator by the output unit 26.

Shown exemplarily in FIG. 3 is a case of application of the mobile function device 10, which in FIG. 3, exemplarily, is used for identifying an emergency situation. The external unit 22 represented in FIG. 3 is realized as a further portable power tool, in particular as a power drill. The mobile function device 10 communicates with the external unit 22 by means of the communication unit 18. For example, a free fall from a ladder by an operator wearing the mobile function device 10 on the arm can be identified by evaluation, by means of the computing unit 14, of at least one operator-specific characteristic quantity and/or position-specific characteristic quantity sensed by means of the sensor unit 12. For example, an acceleration characteristic quantity, sensed by means of the acceleration sensor element 30 of the sensor unit 12, can be evaluated by the computing unit 14.

Immobility following a free fall can likewise be evaluated by the computing unit 14, for example as a result of absence of sensing of an acceleration characteristic quantity by means of the acceleration sensor element 30 of the sensor unit 12. As a result of a communication between the mobile function device 10 and the external unit 22, a plausibility check of the at least one sensed operator-specific characteristic quantity and/or of the at least one sensed position-specific characteristic quantity of the sensor unit 12 of the mobile function device 10, with at least one sensed operator-specific characteristic quantity and/or with at least one sensed position-specific characteristic quantity of the sensor unit 38 of the external unit 20, 22, 24 that can be transmitted from the external unit 20, 22, 24 to the mobile function device 10 by means of the communication unit 18 of the mobile function device 10, can be performed by means of the plausibility unit 16. If the plausibility check likewise produces an identification of a free fall of the external unit 22 and after that an absence of movement, an emergency situation, in particular a fall and unconsciousness of an operator, can be inferred. Clarification may be effected, for example as to whether there is a case of unconsciousness. Sensed vital characteristic quantities such as, for example, a sensed pulse characteristic quantity, that can be sensed by the sensor unit 12, can be evaluated by means of the computing unit 14. By means of the communication unit 18, an accident message and/or hazard message can be sent to an external unit that is realized as a control centre, or transmitted to an external unit (not represented in greater detail here) that is realized as an accident report centre. If communication by means of the communication unit 18 has been deactivated or is not possible, the electronic data can be stored in the storage means 40 of the computing unit 14. The mobile function device 10 can be used, advantageously as a data recorder/accident recorder that stores, for example, accident data.

By means of a communication between the external unit 22, realized as a further portable power tool, and the mobile function device 10, the external unit 22 realized as a further portable power tool can be, for example, switched off atomically, in order to reduce danger to an operator wearing the mobile function device 10 and to avoid possible further injury by the external unit 22 realized as a further portable power tool. Likewise conceivable are further functions, considered appropriate by persons skilled in the art, as a result of a communication between the external unit 22, realized as a further portable power tool, and the mobile function device 10, such as, for example, setting of a protective function in the case of an uncontrolled blockage, or the like.

According to a method for identifying an emergency situation by means of a system 36, a plausibility reconciliation of electronic data, in particular of at least one sensed operator-specific characteristic quantity and/or of at least one sensed position-specific characteristic quantity of the mobile function device 10, and of electronic data, in particular of at least one sensed operator-specific characteristic quantity and/or of at least one sensed position-specific characteristic quantity of the external unit 20, 22, 24, is effected in at least one method step, as has been described exemplarily in the preceding paragraph. In respect of further method steps of the method for identifying an emergency situation by means of a system 36, reference may be made to the rest of the description of the system 36 and/or of the mobile function device 10, since this description is to be construed as also analogous for the method, and consequently all features in respect of the system 36 and/or the mobile function device 10 are also deemed as disclosed with regard to the method for identifying an emergency situation by means of a system 36.

A communication between the mobile function device 10 and an external unit 24, realized as a smartphone, is shown exemplarily in FIG. 4. As a result of a communication between the mobile function device 10 and an external unit 24 realized as a smartphone, electronic data, for example, which are stored in the storage means 40 of the computing unit 14 of the mobile function device 10, can be transmitted to a cloud via the external unit 24 realized as a smartphone. Advantageously, securing of data can be achieved, or the electronic data can be processed further by further units or devices, via the cloud.

What is claimed is:

1. A mobile tool-system function device configured to be disposed on an extremity of an operator, the device comprising:
   a plurality of sensors formed in a housing, the plurality of sensors comprising:
      a first sensor configured to detect a first position-specific characteristic quantity of the mobile tool-system function device, the first sensor comprising an acceleration sensor;
      a second sensor configured to detect an operator-specific characteristic quantity of the operator;
   a communication unit configured to receive a second position-specific characteristic quantity generated and transmitted from a power tool that is external to the mobile tool-system function device; and
   a processor operatively connected to the plurality of sensors, the processor being configured to:
      identify a potential emergency situation based on the first position-specific characteristic quantity from the first sensor, and the second position-specific characteristic quantity from the power tool, the processor being further configured to:
         identify the potential emergency situation as a fall of the operator based on the first position-specific characteristic quantity corresponding to the acceleration sensor detecting an acceleration of the mobile tool-system function device that exceeds a predetermined threshold followed by an absence of acceleration indicating immobility of the operator and based on the second position-specific characteristic quantity corresponding to an acceleration of the power tool that exceeds the predetermined threshold;
identify that the mobile tool-system function device is disposed on the extremity of the operator based on the second sensor detecting the operator-specific characteristic quantity; and
generate an output indicating an emergency situation only in response to identification of the potential emergency situation and identification that the mobile tool-system function device is disposed on the extremity of the operator.

2. The mobile tool-system function device of claim 1 further comprising:
the communication unit being configured to transmit electronic data to an external unit in the power tool used by the operator; and
the processor being further configured to:
transmit the electronic data to the external unit in the power tool to switch off the power tool as the output indicating the emergency situation.

3. The mobile tool-system function device according to claim 1 further comprising:
an output device in the housing; and
the processor being operatively connected to the output device and further configured to:
generate at least one of an optical output and acoustic output indicating the emergency situation.

4. The mobile tool-system function device according to claim 1, the second sensor further comprising:
a temperature sensor configured to measure a body temperature of the operator to identify contact between the mobile tool-system function device and the extremity of the operator.

5. The mobile tool-system function device according to claim 1, further comprising:
at least one fastening unit at least configured to fasten the at least one sensor unit to the extremity of the operator.

6. The mobile tool-system function device according to claim 1, the second sensor further comprising:
a pulse sensor configured to measure a pulse of the operator to identify contact between the mobile tool-system function device and the extremity of the operator.

7. A system comprising:
a power tool configured to be used by an operator, the power tool comprising:
an external unit configured to transmit and receive electronic data; and
a first sensor configure to detect a first position-specific characteristic quantity corresponding to the power tool; and
a mobile tool-system function device configured to be disposed on an extremity of an operator, the device comprising:
a plurality of sensors formed in a housing, the plurality of sensors comprising:
a second sensor configured to detect a second position-specific characteristic quantity of the mobile tool-system function device, the second sensor comprising an acceleration sensor; and
a third sensor configured to detect an operator-specific characteristic quantity of the operator;
a communication unit configured to receive electronic data from the external unit in the power tool and to transmit electronic data to the external unit in the power tool; and
a processor operatively connected to the plurality of sensors and the communication unit, the processor being configured to:
identify a potential emergency situation based on the first position-specific characteristic quantity corresponding to the power tool and the second position-specific characteristic quantity of the mobile tool-system function device, the processor being further configured to:
identify the potential emergency situation as a fall of the operator based on the first position-specific characteristic quantity corresponding to an acceleration of the power tool that exceeds a predetermined threshold and based on the second position-specific characteristic quantity corresponding to the second sensor detecting an acceleration of the mobile tool-system function device that exceeds the predetermined threshold followed by an absence of acceleration indicating immobility of the operator;
identify that the mobile tool-system function device is disposed on the extremity of the operator based on the third sensor detecting the operator-specific characteristic quantity; and
transmit electronic data with the communication unit to the external unit in the power tool to switch off the power tool only in response to identification of the potential emergency situation and identifying that the mobile tool-system function device is disposed on the extremity of the operator.

8. A method for detecting an emergency situation in a system with a mobile tool-system function device configured to be disposed on an extremity of an operator comprising:
receiving, with a processor in the mobile tool-system function device, first sensor data from a first sensor in the mobile tool-system function device configured to detect a first position-specific characteristic quantity of the mobile tool-system function device;
receiving, with the processor, second sensor data from a second sensor in the in the mobile tool-system function device configured to detect an operator-specific characteristic quantity of the operator;
receiving, with the processor and a communication unit in the mobile tool-system function device, third sensor data corresponding to a second position-specific characteristic quantity of a power tool, the third sensor data being generated and transmitted from the power tool that is external to the mobile tool-system function device;
identifying, with the processor, a potential emergency situation based on the first sensor data and the third sensor data, the identifying further comprising:
identifying the potential emergency situation as a fall of the operator based on the first position-specific characteristic quantity corresponding to the acceleration sensor detecting an acceleration of the mobile tool-system function device that exceeds a predetermined threshold followed by an absence of acceleration indicating immobility of the operator and based on the second position-specific characteristic quantity corresponding to an acceleration of the power tool that exceeds the predetermined threshold;

identifying, with the processor, that the mobile tool-system function device is disposed on the extremity of the operator based on the second sensor detecting the operator-specific characteristic quantity; and generating, with the processor, an output indicating an emergency situation only in response to identifying the potential emergency situation and identifying that the mobile tool-system function device is disposed on the extremity of the operator.

\* \* \* \* \*